United States Patent [19]
Carroll

[11] Patent Number: 5,511,273
[45] Date of Patent: Apr. 30, 1996

[54] VARIABLE ENGAGEMENT TOOTHBRUSH

[75] Inventor: David T. Carroll, Schofield, Wis.

[73] Assignee: Preventive Dental Specialties, Inc., Rothschild, Wis.

[21] Appl. No.: 517,791

[22] Filed: Aug. 22, 1995

[51] Int. Cl.⁶ .............................. A47L 13/12; A46B 5/02; A46B 9/04
[52] U.S. Cl. .............................. 15/105; 15/111; 15/143.1; 15/167.1; 433/1; 601/139; 606/235; D4/107
[58] Field of Search .............................. 15/105, 110, 111, 15/143.1, 167.1, 207.2; 119/709, 710, 711; 433/1; 601/136, 137, 138, 139, 141; 606/234, 235; D4/107; D24/194

[56] References Cited

U.S. PATENT DOCUMENTS

| | | |
|---|---|---|
| D. 122,815 | 10/1940 | Crosby . |
| D. 229,903 | 1/1974 | Ceniceros . |
| D. 299,386 | 1/1989 | Jacobs . |
| D. 321,092 | 10/1991 | Woll et al. . |
| 1,826,943 | 10/1931 | Maker . |
| 1,993,662 | 3/1935 | Green .............................. 15/110 |
| 2,121,358 | 6/1938 | Loeffler . |
| 2,273,207 | 2/1942 | Kuhn . |
| 2,826,201 | 3/1958 | Yoder . |
| 3,072,944 | 1/1963 | Clayton .............................. 15/207.2 |
| 3,214,776 | 11/1965 | Bercovitz . |
| 3,669,117 | 6/1972 | Herbst . |
| 3,720,975 | 3/1973 | Nelson . |
| 3,753,266 | 8/1973 | Ceniceros . |
| 4,165,896 | 8/1979 | Hunt . |
| 4,654,921 | 4/1987 | Dinner . |
| 4,888,846 | 12/1989 | Natale .............................. 15/143.1 |
| 5,048,143 | 9/1991 | Carroll . |
| 5,078,732 | 1/1992 | Ceniceros .............................. 15/110 |
| 5,138,737 | 8/1992 | Thomas . |
| 5,272,784 | 12/1993 | Levin . |
| 5,291,878 | 3/1994 | Lombardo et al. . |
| 5,305,490 | 4/1994 | Lundgren .............................. 15/143.1 |

FOREIGN PATENT DOCUMENTS

| | | | |
|---|---|---|---|
| 0813148 | 9/1951 | Germany .............................. 15/167.1 |
| 2727280 | 12/1978 | Germany .............................. 15/110 |
| 687161 | 2/1953 | United Kingdom . |

Primary Examiner—David Scherbel
Assistant Examiner—Randall E. Chin
Attorney, Agent, or Firm—Lathrop & Clark

[57] ABSTRACT

A plastic looped handle has a front ring with two parallel members connected by a front brush head member. Bristles in curved rows extend from one side of the brush head for brushing of teeth, while convex protrusions extend from the other side of the brush head for tongue cleaning. A center bar extends across the front ring, and a rear ring extends rearwardly from the center bar. A front opening is defined between the front ring and the center bar and a rear opening is defined between the rear ring and the center bar. Both openings are sufficiently large to receive at least two human fingers therethrough. The center bar defines an angle with one of the front members of less than 90 degrees, to thereby define a wedge space, into which the hand of a user may be inserted and wedged to thereby retain control of the toothbrush. The two front members are spaced from one another a width to permit the insertion of the brush head into a user's mouth, while the rear ring is substantially wider than the front ring, to thereby permit the support of the brush within the non-extended fingers of a crabbed hand. The brush is particularly suited for use by those who have lost some gripping abilities, and by those who must brush the teeth of others. In addition, by providing black bristles, the brush may be used to brush the teeth of pets.

7 Claims, 3 Drawing Sheets

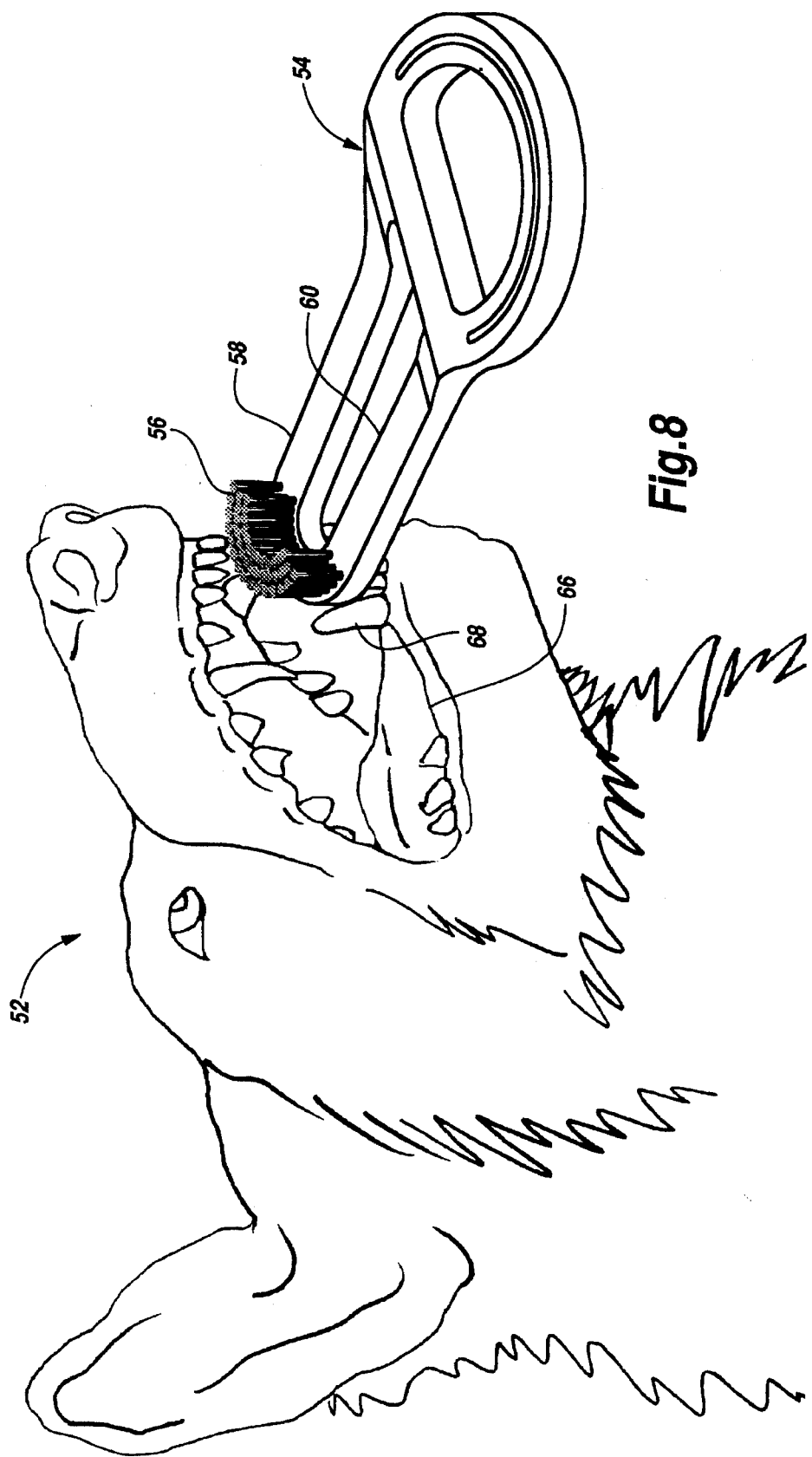

VARIABLE ENGAGEMENT TOOTHBRUSH

FIELD OF THE INVENTION

The present invention relates to oral hygiene devices in general, and to toothbrushes and tongue cleaners in particular.

BACKGROUND OF THE INVENTION

With the growing awareness of the direct link between conscientious oral hygiene and improved dental health, there have been increased efforts by those in all circumstances to institute regular practices for the care and preservation of their teeth. Whereas in earlier times tooth decay and eventual loss were accepted as a given of the ageing process, today even those of advanced age have a rightful expectation of continued possession of their original teeth.

Preservation of teeth from decay, however, is not a matter of incidental or intermittent measures, but is a project requiring daily and perpetual attention and care. The core of an effective regimen of oral hygiene is dally brushing of teeth. Conventional tooth brushes employ an array of tufted bristles disposed at the end of an elongated stick or shaft. For the young and agile, such brushes are entirely adequate, and permit safe and accurate tooth brushing.

Some people, however, lack full hand control, either on a temporary or permanent basis. Arthritis sufferers, those who have experienced trauma to their hands or wrists, and others with sporadic or long-term manipulative difficulties, may find the careful positioning of a stick toothbrush beyond their abilities. They must either forego brushing or brush their teeth haphazardly with conventional brushes, or be required to rely on others for assistance. What is needed is a toothbrush which is easily grasped, even by those of reduced dexterity, which will allow adequate brushing unaided.

Many institutionalized or bedridden persons lack the capacity to brush their own teeth with any tool. For those who must brush the teeth of others, stick brushes are less than adequate, because of the danger that the protruding stick end will strike or damage mouth or gum tissue. For these brush users, a brush which allows noninjurious use and which is particularly adapted for manipulation of the mouths of others is needed.

My earlier U.S. Pat. No. 5,048,143 to a TEETHING BRUSH discloses an advantageous looped brush with particular application with infants and toddlers. What is needed is a brush which further provides control for adults.

SUMMARY OF THE INVENTION

The toothbrush of this invention has a handle with structural members which define openings which permit a variety of modes of engagement between a user's hand and the brush. The plastic looped handle has a front ring with two parallel members connected by a front brush head member. Bristles are arrayed in curved rows and extend from one side of the brush head for brushing of teeth, while convex protrusions extend from the other side of the brush head for tongue cleaning. A center bar extends across the front ring, and a rear ring extends rearwardly from the center bar. A front opening is defined between the front ring and the center bar and a rear opening is defined between the rear ring and the center bar. Both openings are sufficiently large to receive at least two human fingers therethrough. The center bar defines an angle with one of the front members of less than 90 degrees, and defines an angle with the other front member of more than 90 degrees, to thereby define a wedge space, into which the hand of a user may be inserted and wedged to thereby retain control of the toothbrush. By wedging fingers within the handle, users who do not have sufficient strength or dexterity to grasp a brush, for example sufferers of arthritis, may effectively engage the brush for tooth brushing operations. The two front members are spaced from one another a width to permit the insertion of the brush head into a user's mouth, while the rear ring is substantially wider than the front ring, to thereby permit the support of the brush within the non-extended fingers of a crabbed hand. The brush is particularly suited for use by those who have lost some gripping abilities, and by those who must brush the teeth of others, for example nurses and nursing home attendants. In addition, by providing black bristles, the brush may be used to brush the teeth of pets such as dogs.

It is an object of the present invention to provide a toothbrush which may be successfully used by those with limited finger and hand dexterity.

It is also an object of the present invention to provide a toothbrush which may safely be employed to brush another's teeth.

It is another object of the present invention to provide a toothbrush for the brushing of canine and pet teeth.

It is a further object of the present invention to provide a toothbrush for use by those with limited dexterity which also serves as a tongue cleaner.

It is an additional object of the present invention to provide a toothbrush which may be engaged in a variety of fashions to accommodate various levels of hand and finger function.

Further objects, features and advantages of the invention will be apparent from the following derailed description when taken in conjunction with the accompanying drawings.

BRIEF DESCRIPTION OF THE DRAWINGS

FIG. 8 is an isometric view of the brush of FIG. 7 in relation to a dog's teeth.

DESCRIPTION OF THE PREFERRED EMBODIMENT

Referring more particularly to FIGS. 1–8, wherein like numbers refer to similar parts, a toothbrush 20 is shown in FIGS. 1–6. The toothbrush 20 has a handle 22 with specialized structure which allows it to be used by those with limited hand and finger dexterity, and also to be used by attendants for brushing the teeth of those who are incapacitated.

Figure 2:
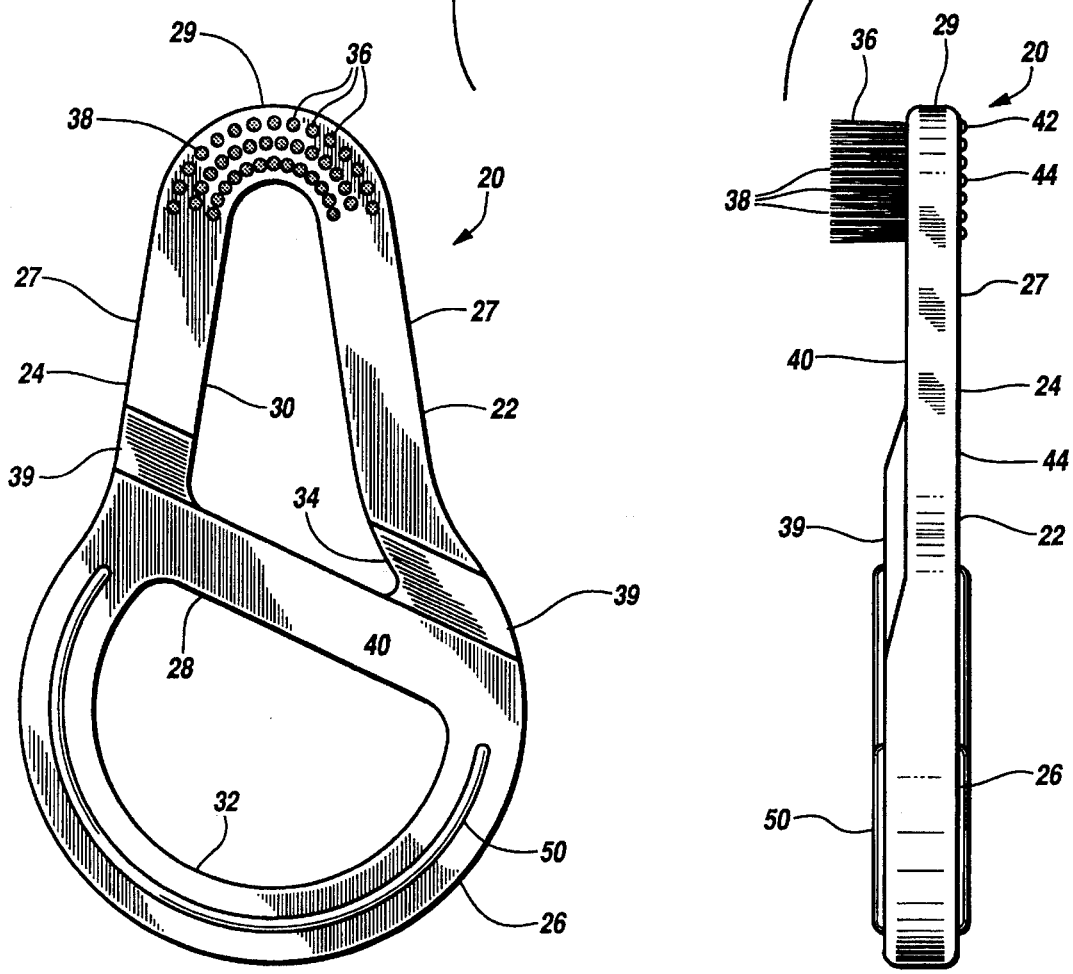
FIG. 2 is a top plan view of the brush of FIG. 1.

As shown in FIG. 2, the brush handle 22 is formed of a forward ting 24 which is connected to a wider rear ring 26. The forward ring 24 is comprised of two generally parallel front members 27 which are joined by a curved brush head 29. The center bar 28 crosses the handle 22 between the forward ring 24 and the rear ring 26 to define a forward opening 30 between the forward ring and the center bar, and a rear opening 32 between the rear ring 26 and the center bar. The center bar 28 is angled with respect to the two generally parallel front members 27, to define an angled wedge section 34. The angle defined between one front member 27 and the center bar is less than ninety degrees, while the angle defined between the center bar and the other front member is greater than ninety degrees, such that as a user's finger or fingers extend further into the wedge section 34, they are more tightly gripped by the brush handle 22. The angled center bar 28 enables a user to fit more fingers in the forward opening 30, then if the bar went straight across. It also gives a longer perimeter of handle on the side toward the users hand which provides greater opportunities for grasping. At the same time, this additional perimeter is provided without unnecessarily widening or lengthening the brush, which must be confined to dimensions suitable for insertion in a user's mouth.

The width of the forward ring 24 is sufficiently narrow to allow the insertion of the brush head into an adult's mouth. The range of widths is from about one-and-a-quarter inches to about one-and-three-quarters inches, and is preferably about one-and-a-half inches. The width of the forward opening 30 is preferably at least three-quarters of an inch to permit at least two fingers to be inserted into the opening 30. The rear ring 26 is about 5/16 inches thick to provide a stiff and easily graspable segment, while the forward ring 24 is preferably of reduced thickness, for example 4/16 inches. A tapered segments 39 form a smooth transition between the thicker rear ring 26 and the thinner forward ring 24.

The brush handle 22 is preferably molded of a plastic resin such as polypropylene and has radiused intersections to remove sharp edges which might traumatically engage regions of the mouth.

Figure 3:
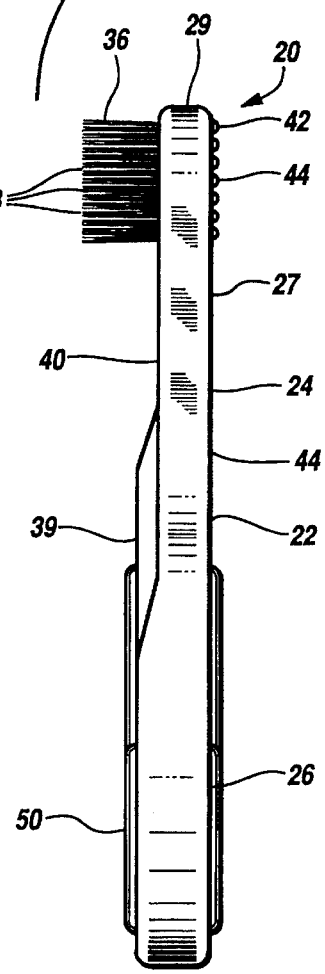
FIG. 3 is a side elevational view of the brush of FIG. 1.

The brush head 29 of the forward ring 24 supports three curved rows of tufts 36 of bristles 38. The bristles 38 are mounted in a conventional manner to the handle 22, such as by stapling into the handle plastic, and may be formed of a plastic material such as TYNEX®nylon, manufactured by E. I. Du Pont de Nemours and Company, of Wilmington, Del. Because of the preferred curved configuration of the tufts 36, the forwardmost row of bristles will typically have a greater number of tufts than the rearward rows. For example, the front row may have fifteen tufts, the middle row 14 tufts, and the rear row 13 tufts. The tufts 36 extend upwardly from the top surface 40 of the brush handle 22, as shown in FIG. 3.

A plurality of small convex protrusions 42 extend downwardly from the bottom surface 44 of the brush handle 22. These protrusions 42 form a tongue-cleaning array 44 disposed beneath the bristles 38 and positioned for engagement with a user's tongue. The protrusions 42 when run gently over the surface of the tongue, serve not only to dislodge odor-causing bacteria and other tongue-situated debris, but also serve to stimulate the tongue papillae to produce additional saliva. Saliva flow, which is typically reduced in older persons, is desireable to confront the presence of bacteria which cause tooth decay.

Figure 4:
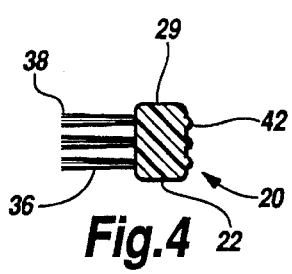
FIG. 4 is a cross-sectional view of the brush of FIG. 7 taken along section line 4—4.
Figure 6:
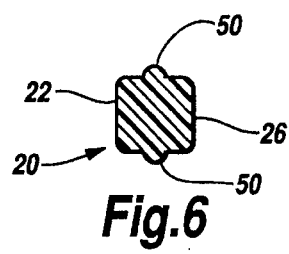
FIG. 6 is a cross-sectional view of the brush of FIG. 7 taken along section line 6—6.
Figure 5:
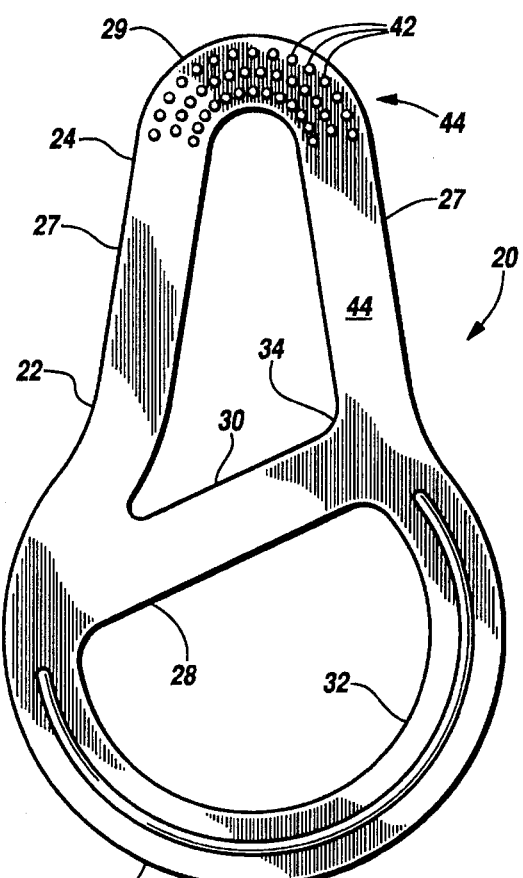
FIG. 5 is a bottom plan view of the brush of FIG. 1.
Figure 7:
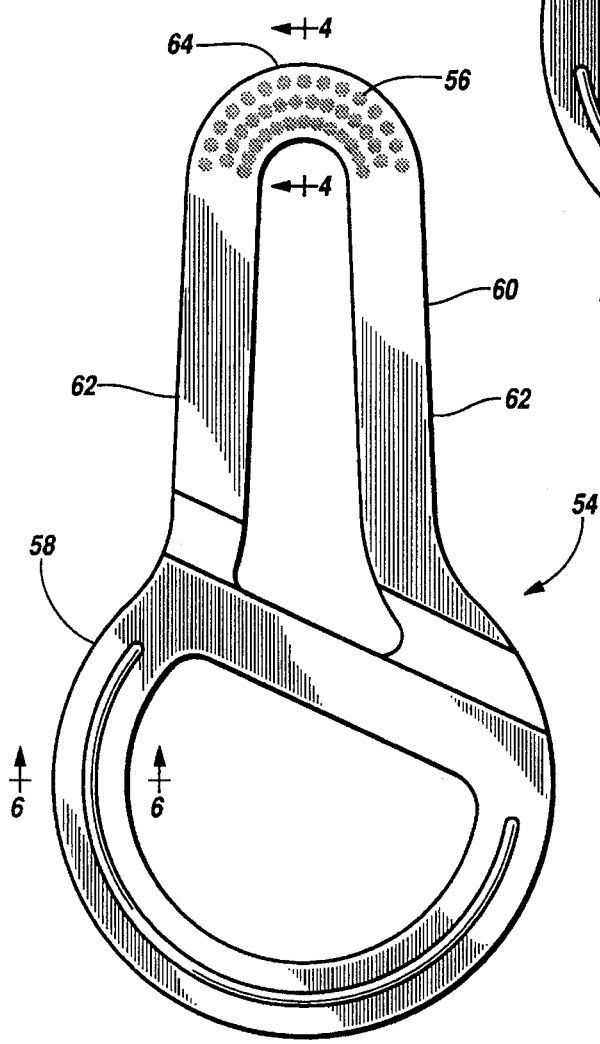
FIG. 7 is a top plan view of an alternative embodiment brush of this invention for use in brushing the teeth of pets.

To further assist with frictional engagement between a user's hand and the brush 20, a substantially continuous ridge 50, shown in FIGS. 2 and 4, extends along the rear ring and extends from both the top surface 40 and the bottom surface 44.

Figure 1:
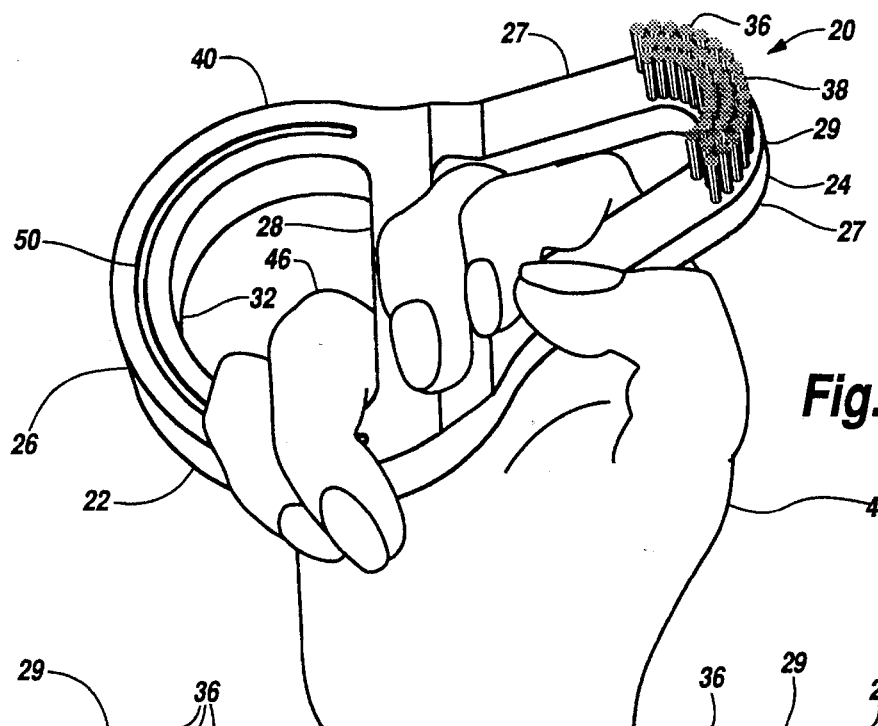
FIG. 1 is an isometric view of the brush of this invention gripped by a user with limited hand dexterity.

As best shown in FIG. 1, the openings of the brush handle 22 provide variable means for engaging the brush 20 with the fingers 46 of a user's hand 48. A user may place one or two fingers in the forward opening 30, with the remainder in the rear opening 32. Although the fingers in the rear opening will not be wedged in place, the fingers in the forward opening may be wedged in place to insure effective engagement between the brush 20 and the user's hand, even if it is not possible to clasp the brush by contracting the grip of the fingers. In addition, the center bar 28 is frictionally engaged between the fingers in the front opening and the fingers in the rear opening.

Alternatively, for those users who are uncomfortable with inserting fingers in the openings, the narrow forward ring 24 and the substantially wider rear ring 26 work together to allow a user with crabbed fingers, or whose fingers remain constantly contracted, to cradle the brush 20 so that the brush head protrudes from the hand between the thumb and the index finger, with the rear ring 26 backed and supported by the remaining fingers.

It should be noted that although the illustrated brush 20 has been shown with the center bar 28 inclined from a forward to a rear position to more effectively accommodate a right-handed person, the inclination of the center bar 28 may be reversed to accommodate a left-handed person.

Even for those who do not suffer from finger dexterity loss, the same gripping mechanisms may be employed when utilizing the brush 20 for brushing the teeth of others. The rounded brush head 29 reduces the chance that the brush will be over-inserted to harshly impact mouth tissue. In addition, when it is desired to inspect the teeth and mouth of an incapacitated person, it is necessary only to rotate the brush 20 so that one of the forward members engages the upper teeth, and one forward member engages the lower teeth. The jaws are thereby gently propped open permitting a view into the interior of the mouth.

Another application where a user is brushing the teeth of another is illustrated in FIG. 8, where a modified brush 54 is used for brushing the teeth of a pet, such as a dog 52. The brush 52 may be identical to the brush 20, except for the provision of dark, preferably black, bristles 56. However, in the embodiment 52 shown in FIG. 7, the brush has a handle 58 with an extended front ring 60 having front members 62 which are more nearly parallel to one another and joined by a curved brush head 64. Canine jaws are substantially more parallel to one another than human jaws, hence the front ring 60 with its approximately parallel front members may be inserted in the mouth 66 of the dog 52 and used to separate the jaws and permit the inspection of the dog's teeth.

The black bristles 56 stand in stark contrast to the white of the dog's teeth 68. This contrast allows a pet owner to exercise care in cleaning the dog's teeth, allowing a visual guide to the proper placement of the moving bristles. Furthermore, the dark bristles will allow the material alba which is removed by the brushing action to be displayed on the bristles, and to thereby give the owner an indication of the state of cleanliness of the pet's teeth.

It is understood that the invention is not limited to the particular construction and arrangement of parts herein illustrated and described, but embraces such modified forms thereof as come within the scope of the following claims.

I claim:

1. A toothbrush comprising:
   a front ring having two frontwardly extending front members connected by a front brush head member;
   b) a plurality of bristles which extend upwardly from the front brush head member;
   c) a rear ring;

d) a center bar which extends between the front ring and the rear ring, wherein a front opening is defined between the front ring and the center bar, and the front opening is large enough to receive at least two human fingers therethrough, and wherein a rear opening is defined between the rear ring and the center bar, and the rear opening is large enough to receive at least two human fingers therethrough; and wherein the center bar defines an angle with one of the front members of less than 90 degrees, and defines an angle with the other of said two front members which is greater than 90 degrees, to thereby define a wedge space, into which the fingers of a user may be inserted and wedged to thereby retain control of the toothbrush.

2. The toothbrush of claim 1 further comprising a substantially continuous ridge which extends along the rear ring and which extends from a surface opposite the bristles, to thereby provide improved grip between a user's hand and the handle.

3. The toothbrush of claim 1 wherein the two front members are spaced from one another a width to permit the insertion of the brush head into a user's mouth, and wherein the rear ring is substantially wider than the front ring, to thereby permit the support of the brush within the non-extended fingers of a crabbed hand.

4. The toothbrush of claim 1 wherein the bristles are black to thereby provide color contrast between the white teeth of a pet and provide a visual guide to the brushing thereof.

5. The toothbrush of claim 1 further comprising a plurality of convex protrusions extending from the front ring beneath the bristles, said protrusions being engageable with the tongue of a user to thereby serve as a tongue cleaner.

6. A toothbrush comprising:
  (a) a front ring having two frontwardly extending front members connected by a front brush head member;
  b) a plurality of bristles which extend upwardly from the front brush head member;
  c) a rear ring;
  d) a means for engaging a user's fingers which extends between the front ring and the rear ring, wherein a front opening is defined between the front ring and the means for engaging, and the front opening is large enough to receive at least two human fingers therethrough, and wherein a rear opening is defined between the rear ring and the means for engaging, and the rear opening is large enough to receive at least two human fingers therethrough; and wherein the means for engaging is defined by a center bar which defines an angle with one of the front members of less than 90 degrees, and defines an angle with the other of said two front members which is greater than 90 degrees, to thereby define a wedge space, into which the fingers of a user may be inserted and wedged to thereby retain control of the toothbrush.

7. A toothbrush for brushing the teeth of an animal, the toothbrush comprising:
  a) a handle having a front ring, a rear ring, and a center bar which extends between the front ring and the rear ring, wherein a front opening is defined between the front ring and the center bar, and the front opening is large enough to receive at least two human fingers therethrough, and wherein a rear opening is defined between the rear ring and the center bar, and the rear opening is large enough to receive at least two human fingers therethrough wherein the front ring has two front members which extend forwardly from the center bar, and wherein the center bar defines an angle with one of the front members of less than 90 degrees, and defines an angle with the other of said two front members which is greater than 90 degrees, to thereby define a wedge space, into which the fingers of a user may be inserted and wedged to thereby retain control of the toothbrush; and
  b) a plurality of bristles which extend upwardly from the front ring, wherein the bristles are black to stand in sharp contrast to the light color of the brushed animal teeth.

* * * * *